(12) United States Patent
Crespi et al.

(10) Patent No.: US 7,570,996 B2
(45) Date of Patent: Aug. 4, 2009

(54) COMPLEX-SHAPED CERAMIC CAPACITORS FOR IMPLANTABLE CARDIOVERTER DEFIBRILLATORS AND METHOD OF MANUFACTURE

(75) Inventors: Ann M. Crespi, Mobile, AL (US); John D. Norton, New Brighton, MN (US); Frank A. Duva, Carlsbad, CA (US)

(73) Assignee: Medtronic, Inc., Minneapolis, MN (US)

( * ) Notice: Subject to any disclaimer, the term of this patent is extended or adjusted under 35 U.S.C. 154(b) by 550 days.

(21) Appl. No.: 11/348,681

(22) Filed: Feb. 7, 2006

(65) Prior Publication Data

US 2006/0126265 A1 Jun. 15, 2006

Related U.S. Application Data

(62) Division of application No. 10/426,680, filed on Apr. 30, 2003, now abandoned.

(51) Int. Cl.
*A61N 1/00* (2006.01)

(52) U.S. Cl. .......................................................... 607/9

(58) Field of Classification Search ..................... 607/9; 73/718; 29/25.42, 595, 602.1
See application file for complete search history.

(56) References Cited

U.S. PATENT DOCUMENTS

| | | | |
|---|---|---|---|
| 3,815,187 A * | 6/1974 | Hanold, III | 29/25.42 |
| 4,991,283 A * | 2/1991 | Johnson et al. | 29/595 |
| 5,317,919 A * | 6/1994 | Awtrey | 73/718 |
| 6,169,925 B1 | 1/2001 | Villaseca et al. | |
| 6,240,317 B1 | 5/2001 | Villaseca et al. | |
| 6,345,434 B1 * | 2/2002 | Anbo et al. | 29/602.1 |
| 6,456,256 B1 | 9/2002 | Amundson et al. | |
| 2002/0065539 A1 | 5/2002 | Von Arx et al. | |

* cited by examiner

*Primary Examiner*—George Manuel

(57) ABSTRACT

An improved manufacturing and packaging process for optimizing the size of various implanted medical devices is disclosed. Specifically, complex shapes involving ceramic capacitors with various other shapes are manufactured to optimize fit and shapes within the device housing. The manufacturing process includes various techniques and electrode material selections, including manufacturing processes that enable high energy discharge capacitors to be made in compliant shapes to fit in small ICD footprints.

15 Claims, 4 Drawing Sheets

COMPLEX-SHAPED CERAMIC CAPACITORS FOR IMPLANTABLE CARDIOVERTER DEFIBRILLATORS AND METHOD OF MANUFACTURE

PRIOR APPLICATIONS

This application is a divisional application of U.S. Ser. No. 10/426,680, filed Apr. 30, 2003 now abandoned, entitled "Complex-Shaped Ceramic Capacitors for Implantable Cardioverter Defibrillators and Method of Manufacture", which is herein incorporated by reference in it's entirety.

FIELD OF THE INVENTION

An energy storage and delivery component for an implantable medical device having component external features which are conformal to surrounding components or housing in the medical device.

BACKGROUND OF THE INVENTION

Implantable Cardioverter Defibrillators (ICD's) have decreased substantially in volume in recent years, but are still larger than desirable. The high energy discharge capacitors that create the defibrillation pulse are typically the largest components in the device, normally at about 12 cubic centimeters for a 30 Joule device. In addition to small size, it is desirable for the ICD to have a curved profile for patient comfort. As the curved ICD shrinks in size, it becomes more and more necessary for internal components to also be curved to achieve a volume-efficient design.

Defibrillators with aluminum electrolytic capacitors that have a curved profile are currently in use. These capacitors have a "D"-shape which generally fits into the curved bottom or side of the defibrillator can. However, these capacitors are still larger than desirable, and are not likely to reach more than about 4-5 Joules per cubic centimeter in volumetric energy density. "D"-shaped tantalum capacitors for ICD's have also been reported. These capacitors are slightly higher in volumetric energy density than aluminum electrolytic capacitors, but they are much heavier. The weight of these are about 6 grams per cubic centimeter in a finished capacitor.

Another class of capacitors include those generally referred to as ceramic capacitors. Although within that general class there are different constructions, one of these includes the lead lanthanum zirconium titanate (PLZT) ceramic construction. PLZT ceramic capacitors may be useful as high energy discharge capacitors for implantable cardioverter defibrillators. These capacitors are capable of energy densities as high as about 7 Joules per cubic centimeter, compared to about 2.5 to 3 Joules per cubic centimeter that is currently available.

SUMMARY OF THE INVENTION

D-shaped capacitors such as the aluminum electrolytics and the tantalums have been manufactured with a straight edge perpendicular to the curve of the D, rather than with a compound radius such as in some batteries within implantable medical devices. Since it is highly desirable for the ICD to have a compound radius forming its outer housing, it is also desirable for the capacitor to have a compound radius so the radius space can be efficiently utilized. This may be accomplished with the present invention by using chip portions of the capacitor having graduated shapes and stacking or ranging the largest chips in the middle and the smallest on the outside. Alternatively, a further reduction in volume may be achieved by milling the edges of the chipped portions so that they are sloped rather than at a 90° or similar angle.

The three largest components in ICD's today are the capacitors, the battery, and the electronics module. The shapes that are possible with each of these components dictates which mechanical designs are feasible. With the current invention, there is greater flexibility of mechanical design for the capacitor, which in turn opens up new possibilities for ICD layout. In one example, a capacitor may be made with a step structure which may overlay another component such as a battery or electronics module. In another embodiment, in view of the capacitor being made of discrete chips having optional differences in sizes, it is not necessary to have the capacitor as a single large component. Rather, it is possible now with this technology to create a number of parts having different shapes and sizes which may be distributed throughout the device in spaces that are otherwise hard to utilize with other component shapes.

It is possible, therefore, to manufacturer an implantable cardioverter defibrillator having at least one capacitor by use of a process including the steps: of providing at least one print pattern for a capacitor to a tape casting and screen printing process; applying a first layer of electrode material onto portions of the print pattern; and creating a stack by applying at least one additional layer of electrode material onto portions of the print pattern after first reversing the print pattern by 180° between each layer application so that the rotation and applying steps creates adjacent terminals on the same side of the capacitor.

In another embodiment, a capacitor may be manufactured by following certain other steps. A plurality of print patterns is provided for at least one capacitor to a tape casting and screen printing process. A first layer of electrode material is then applied onto portions of the print patterns, and a plurality of stacks are created each having a plurality of layers forming chips by applying at least one additional layer of electrode material onto portions of the print patterns. The at least one additional layer is applied after first reversing the print patterns by 180° between each layer application so that the rotation and applying steps creates additional terminals on the same side of the capacitors. The stacks are then laminated at high pressure and a portion of at least one of the stacks is then removed in a manner which alters the shape of a portion of the at least one stack from the original print pattern. A cut line is located on the print pattern in each stack and the capacitor stacks are cut through the cut line between upper and lower surfaces to create portions of the pattern in which at least two chips have difference sizes or shapes. The chips are then processed in normal course, and are partially rotated and then assembled to form various chips as new full capacitor stacks in which the orientation of the portions is different than in the original portions and the shape of the new full capacitor stacks are different than in the initial print pattern.

The invention also includes an implantable cardioverter defibrillator device which comprises at least one capacitor for storing and delivering electrical energy on demand. The capacitor has at least a 30 Joule capacity and a volumetric energy density of at least about 5 Joules per cubic centimeter. The at least one capacitor has outer surfaces which conform and shape to adjacent components or housing walls, with the outer surfaces comprising a plurality of ceramic chips which do not all have the same aspect ratio.

DETAILED DESCRIPTION OF THE INVENTION

The invention relates to improved manufacturing and packaging know-how, and techniques for optimizing the size of various implantable medical devices without diminishing the power capacity of those devices. In particular, this invention permits certain components to be manufactured in a way to optimize the packaging relating to curved surfaces of device housings and optimizing fit in and among other component shapes within the device. In one embodiment of this invention, ceramic capacitors are provided which are manufactured using various techniques and electrode material selections, but as a minimum including certain features of manufacturing and process steps which enable high energy discharge capacitors to be made in shapes that will allow them to fit in very small ICD footprints. Accordingly, the invention enables efficient manufacture of very small ceramic capacitors with curved or other shaped edges that provide more practicality to meet the demand of today's ever smaller and curved housing-shaped ICD's. The invention further enables manufacture of more complex shapes than are practical or possible in an aluminum electrolytic capacitor, which is housed in a metal can. For example, welding and assembly requirements limit the shapes possible for such a capacitor. In contrast, the individual chips formed using the processes enabled herein may be made into a wide variety of shapes and can be either joined together or dispersed throughout the device to use space most efficiently.

Figure 1:
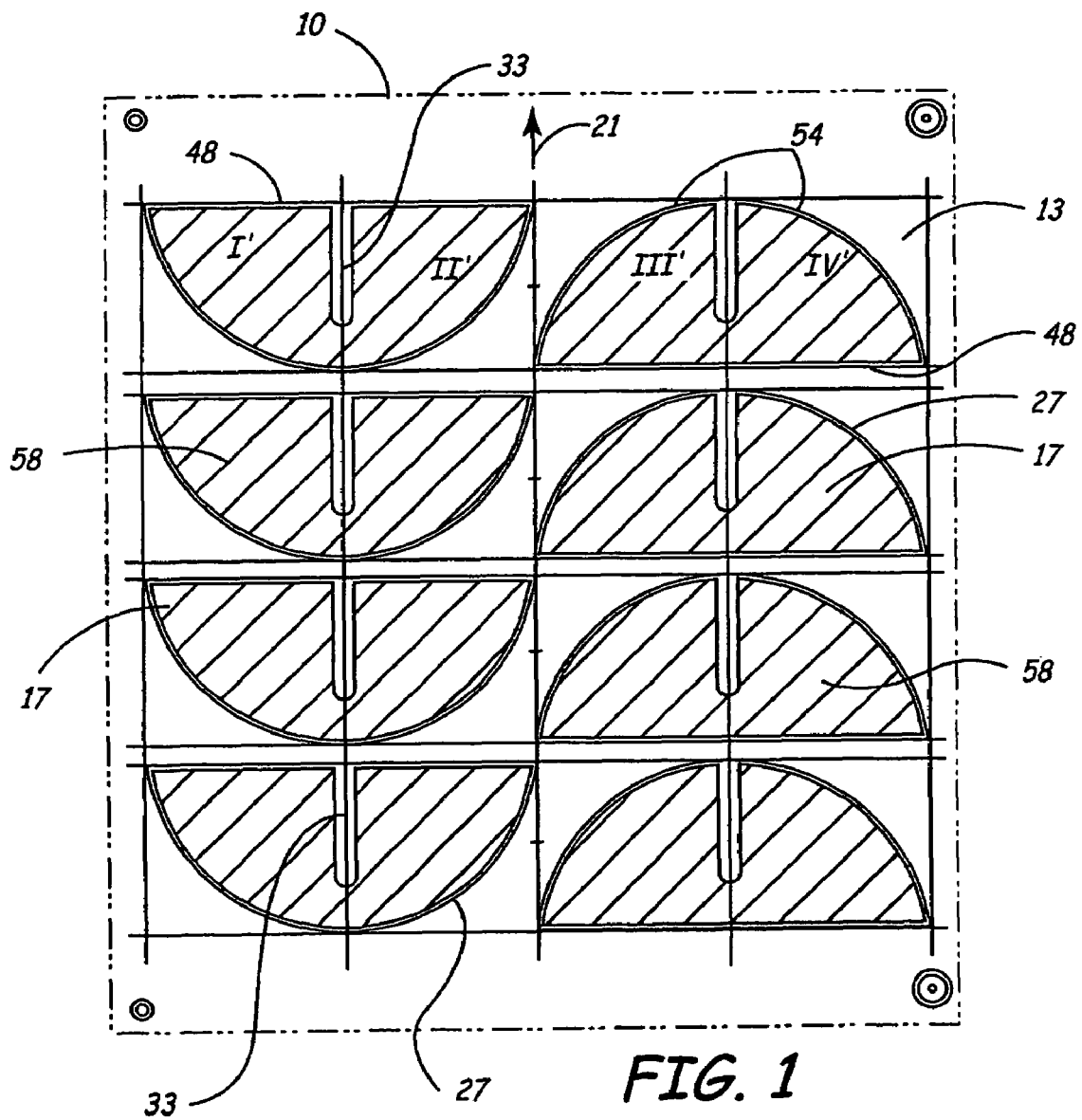
FIG. 1 is a top plan view of a tape casting process bar having a plurality of print patterns shaped as capacitor shapes and with a first electrode material layer shown.

In one embodiment, the process for making such capacitors of the present invention involves a 180° reversal of the bar between prints of the metallic electrodes in order to make alternate layers of opposite polarity. As is known in the tape casting and screen printing industry, and as shown in FIG. 1, bar 10 comprises a medium upon which is placed a print pattern to guide the application of material during the subsequent process steps. In this example, print pattern 13 generally includes a plurality of capacitor-like shapes 17 forming part of the print pattern. In the process, the bar, upon which is a print pattern, is advanced through a process line to receive layers, including electrode material, on portions of the print pattern. The advancement may be along the direction arrow 21, which merely represents an exemplary direction for further reference.

In each capacitor shape 17, there is shown a border area 27 bounded within the double lines within which there is no metallic ink or electrode material that is printed and thereby has formed an insulating ceramic margin. It should be noted that although the shape 17 is generally that of a D-shape, the invention is not so limited to a specific shape. However, there is also shown a deep U-shaped area 33 (although again the shape is not as critical as the function) which is, in this embodiment, near the center portion of the capacitor shape on the print pattern. The area within the U-shape is designed to remain free of electrode material as well. As will be shown, the areas directly below the shape margin will facilitate formation of termination areas on a subsequently configured capacitor stack. Two of the capacitor shapes are labeled with numerals I', II', III' and IV'. These generally depict half portions of specific capacitor shapes shown on the bar of FIG. 1, and will be useful for tracking the sequence of orienting these portions in subsequent figures. In FIG. 1, the rectangular shape having numerals I'/II' has the U-shaped area opening towards the straight edge 48, whereas the capacitor shape having portions III' and IV' has U-shape opening towards the radius or non-linear surfaces 54. Lines 58 generally indicate that bar 10 has progressed through the processing to a point at which at least one layer of electrode material 58 has been applied to portions of the print pattern 13.

Figure 2:
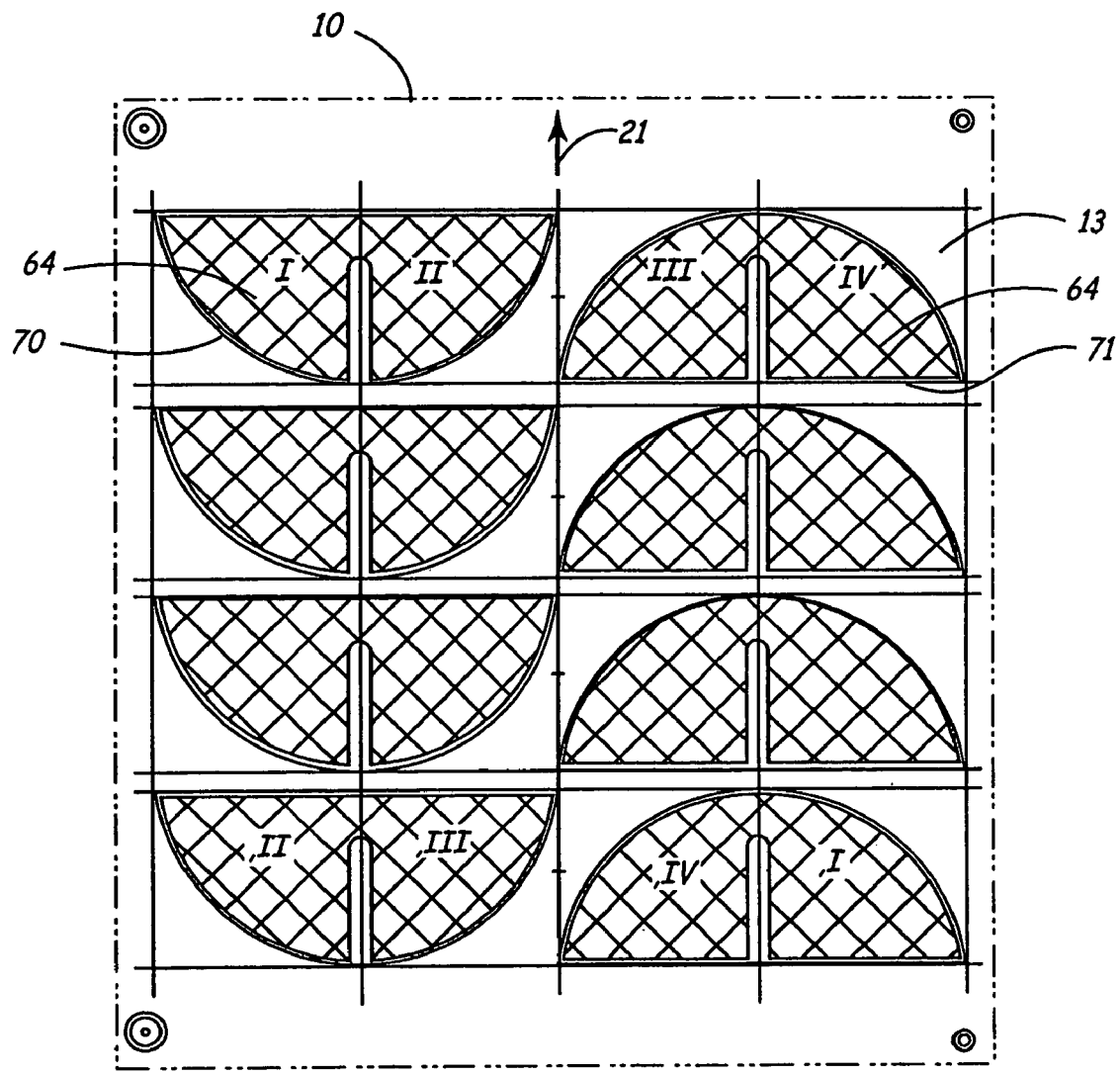
FIG. 2 is a top plan view of the bar of FIG. 1 after bar reversal and application of a second layer of electrode material.

FIG. 2 illustrates bar 10 continuing to proceed in direction 21 through the processing line, however bar 10 has been reversed by 180° as can be seen by the orientation of newly designated capacitor shapes I, II, III, and IV. It is recognized that process steps describing this bar reversal technique may be variously described. Also, it is contemplated that certain improvements might accrue to less than a 180° reversal. Regardless, as shown in FIG. 2, there is also then applied at least one additional layer of electrode material, shown here as lines 64. Once again, it is recognized that lines 58 and 64 are merely representative of layers applied to the designated portions of the print pattern of the bar. It is further understood that the term "layer" may comprise a wide array of layer depths and other characteristics of the electrode material, consistent with the functional requirements of the intended component and device. It is recognized that, in some embodiments, the term "layer" may have a wide meaning and may not comprise a symmetric coating in cross-section or density, volume, or location.

Figure 3:
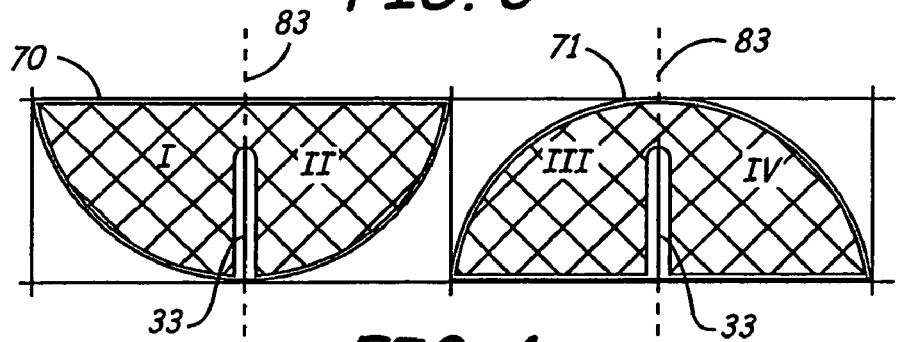
FIG. 3 is a portion of the bar of FIG. 2.

What is shown, therefore in FIGS. 1 and 2 is the creation of a capacitor stack in which a specific process includes providing the initial print pattern for at least one capacitor within a tape casting and screen printing process. Then, a first layer of electrode material 58 is applied on to portions of the print pattern 13. Finally, a stack is commenced by applying at least one additional layer 64 of electrode material onto portions of the print pattern after first reversing the print pattern by 180°, and continuing to implement such reversals of the bar between each layer application so that the rotation and applying steps creates adjacent terminals on the same side of the capacitor, once formed. In one embodiment, the layering process is repeated until about 20-50 layers are created. However, other amounts of layers are also contemplated within the scope of the invention. FIG. 3 depicts only a portion of the bar shown in FIG. 2 in which the two designated capacitor shapes 70, 71 are highlighted for illustration. FIG. 3 also identifies a cut line 83, which in this embodiment is also a center line of the pattern.

Several processes may be used for making ceramic capacitors. The present invention is adaptable to any of these processes. For example, a tape process may be implemented to construct the various elements of the present invention. This process uses wet slurry, which is cast on a belt of various materials, such as stainless steel or mylar, and the thickness of the cast tape is controlled by a doctor blade, viscosity and speed control device or equivalent. Specifically, a wet film is cast on a belt, processed through a drying oven or chamber to remove solvents within the slurry to produce a thin film or ceramic material. The ceramic is held together with a binder and may have a thickness ranging from a few microns to several thousands. The cast tape can be of different widths, depending upon subsequent printing equipment. The cast tapes may be removed from the belt carrier or can remain on the belt as it is processed through the printing stage. Subsequently, a print pattern is screened or applied to the cast tape by various means, but the result is always a printed pattern that eventually makes up a capacitor. After the cast tape is printed, another piece of dried cast tape is placed on top of the printed pattern and another pattern is applied to the surface of the tape. This process is repeated as many times as needed to build the desired capacitor and the predetermined capacitance value. After the stack is completed, a thermal compression method (lamination) is performed to form a relatively solid block and prevent the stack from coming apart at the tape interfaces. Since the cast tape printed patterns are generally more than one per tape section, cutting or singulation is required.

Yet another process that may be used is a wet process. This process is also referred to as wet cast, wet printing and/or waterfall process. These processes are essentially the same or similar to the dry tape process in that a film of wet ceramic is deposited on a carrier. The deposition can be wet cast, similar to the dry tape process, wet printed through a stainless steel screen or flowed. The wet film is dried similar to the tape process. A metal pattern is then deposited on the dried film. Instead of placing another dried section of tape on the printed layer, another wet film is deposited directly on the first printed wet film that has been dried. Thereafter, the second film is dried, printed upon or has a print deposited upon it. The print is dried, and the process repeated for as many times as required. No lamination is needed under the wet process. Similar to the tape process, cutting or singulation is needed.

Figure 4:
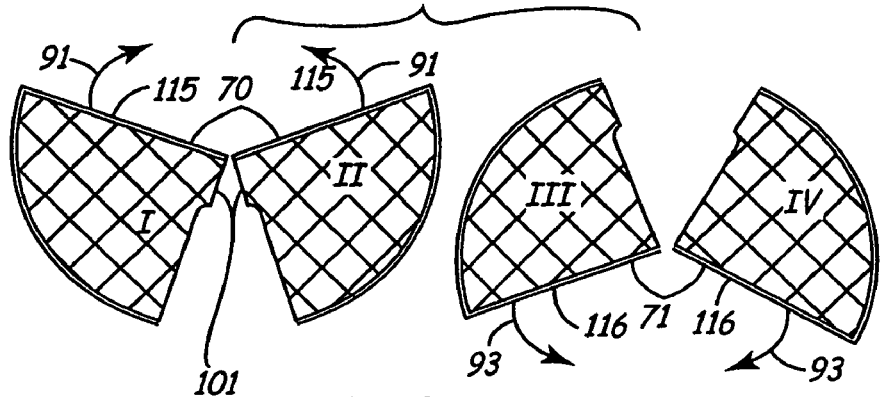
FIG. 4 is a top plan view of two of the capacitor print patterns after cutting and at the commencement of re-orienting.
Figure 5:
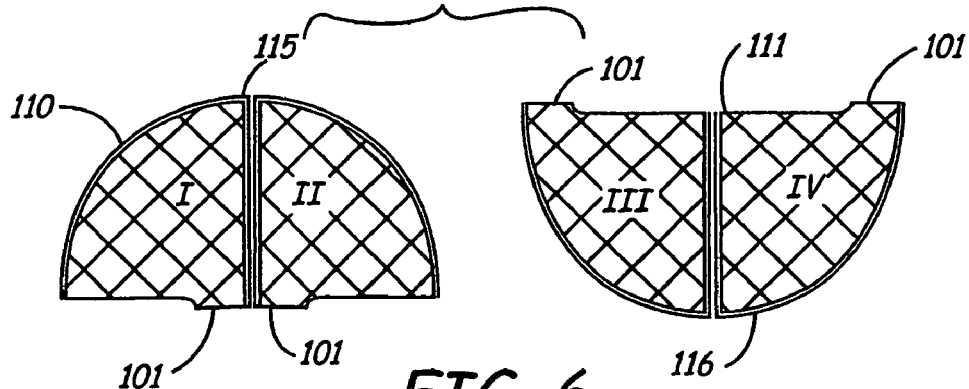
FIG. 5 is a top plan view of the portions of the cut stack shown in FIG. 4 in a re-oriented configuration.
Figure 6:
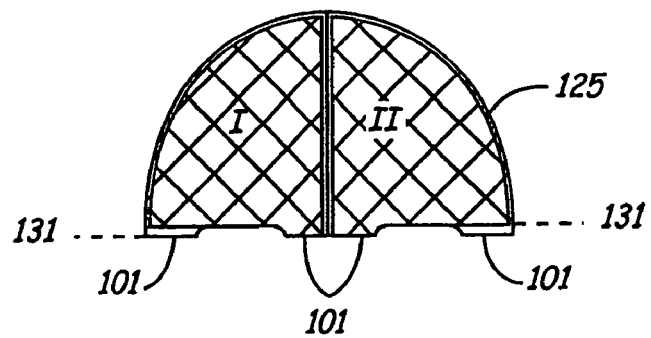
FIG. 6 is a top plan view of the stacked portions of FIG. 5 combined in an overlaying fashion.

In one embodiment, it is then desirable to take the configurations of FIG. 3 and cut or otherwise remove them from the bar. The result will be a plurality of stacks of capacitor shapes (with the areas 33 also removed) which may then be configured for further processing, such as lamination at high pressure. One or more stacks may then be processed further according to the invention. FIG. 4 illustrates an example of the two stacks of FIG. 3 which are being prepared for re-orientation of the portions labeled I, II, III, and IV. As shown in FIG. 4, a separation or cut along cut lines 83 was made resulting in creation of, in this embodiment, two half portions for each of the capacitor stacks 70, 71. These half portions are then rotated in the direction of lines 91, 93. The earlier bar rotation of 180° enabled creation of opposing terminals 101 configured adjacent to each other on the same side of the capacitor stack. This is an improvement over prior known technologies in that it obviates the need for creation of terminals on opposite sides as in conventional ceramic capacitors. It is recognized that, in certain embodiments, the portions shown in FIG. 4 are further processed according to well known techniques relating to binder burnout, firing, termination, burn-in, and acceptance testing. However, the rotation step shown in FIG. 4 is then implemented and completed as shown in FIG. 5 to form newly oriented half portions comprising newly shaped capacitor stacks 110, 111. These stacks have terminations 101 configured as shown, and which then will be further combined in various manner, such as for example that shown in FIG. 6. The half portions (or in asymmetrically configured cuts in alternate embodiments, the portions that result from the cut) are then glued together or otherwise joined, for example by use of epoxy or other suitable material. The joining occurs at the flat, non-terminated edges 115, 116, which results in the terminations being configured at a plurality of locations on the stack. In the embodiment shown in FIGS. 4-6, the particular cut line and particular shape of area 33 results in terminations being configured along generally the same side of a resulting capacitor stack, such as combination stack 125, shown in FIG. 6. Combination stack 125 is simply the combination of smaller stack portions, for example chips represented as shown in FIG. 5 by stacks 110, 111 which are then overlaid into a combined stack 125. As shown in FIG. 6, the two terminals forming the center portion along edge 131 may be utilized for one polarity, and the two terminals at the outside of edge 131 will be joined to make the other polarity.

Figure 7:
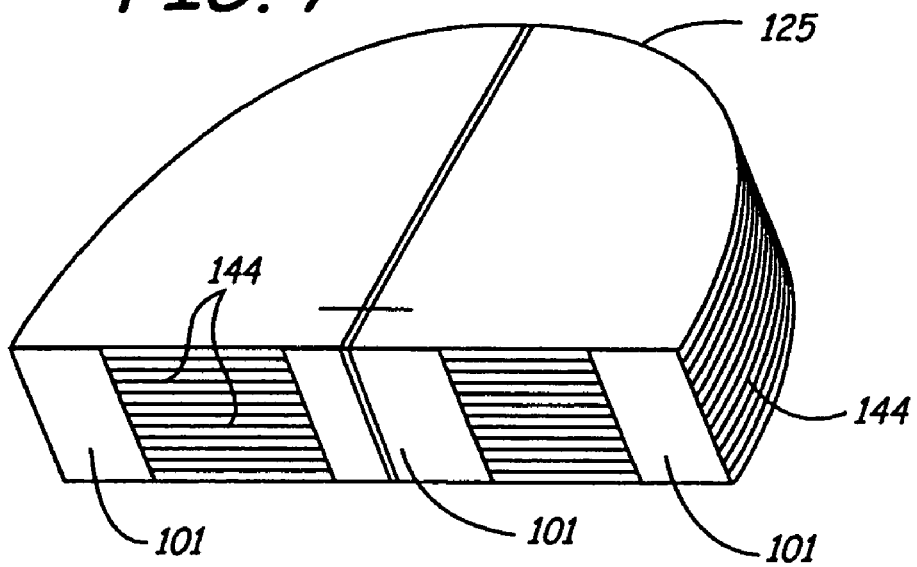
FIG. 7 is a perspective elevation view of a capacitor stack embodiment of the invention.
Figure 8:
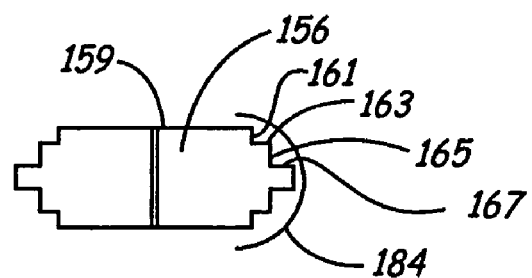
FIG. 8 is a schematic side elevation view of side surfaces of a capacitor manufactured according to at least one embodiment of this invention shown in conformal fit with a housing compound angle.
Figure 9:
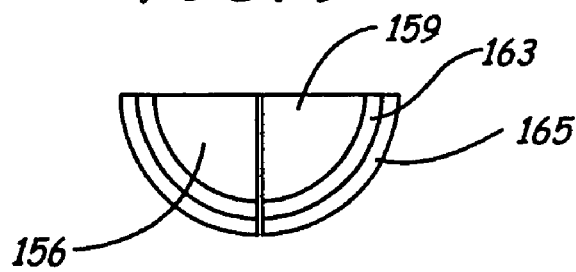
FIG. 9 is a top plan view of the capacitor depicted in FIG. 8.

FIG. 7 is a perspective elevation view of a schematic depiction of a capacitor stack 125 substantially as shown and described in relation to FIG. 6. Although FIG. 7 illustrates a novel complex shape which provides improved efficiencies for capacitor and component level manufacturing, FIG. 7 depicts a generally uniformly shaped arrangement of stacked chips 144 within the capacitor stack. It may be desirable to utilize different cut lines as well as different techniques for removing or re-shaping portions of chips within the capacitor stack during the processing in order to result in a more complex shape of capacitor stack. This would enable yet further improvements in packaging such stacks in relation to the compound radius or irregular shapes of device housings, such as shown in FIG. 8, and which will be further described below, as well as for packaging more efficiently in relation to other components within a device. For example, aspect ratios of capacitors and other components formed according to this technology may have one or more notches, steps, or other shapes creating compound aspect ratios. FIG. 8 is a schematic side elevation view of capacitor 156 having outer surfaces 159, 161, 163, 165, 167 and other similar surfaces. These are formed, for example, using the methods and techniques disclosed herein to create a complex outer shape which is customizable for improved fit within the shape of housing 184 or other adjacent structure. FIG. 9 is a top plan schematic view of capacitor 156 illustrating the multiple surfaces formed by milling or other processes as disclosed or suggested herein.

In addition to improved space efficiency for packaging purposes, it is also possible to utilize this technology to create efficient stacking structures that enable improved utilization of multiple capacitor components and/or capacitors distributed throughout the device, rather than in a single location or block, and provide improved packaging efficiency over current multiple capacitor configurations. The technology also enables use of capacitor chips on flexible tape to realize further efficiencies in the manufacturing and assembly processes. What is provided, therefore, is a novel technology which, through certain processes, produces capacitors with outer surfaces that do not all have the same aspect ratio. When used in an implantable cardioverter defibrillator or other energy demanding devices, such capacitors enable improved packaging efficiencies as well as improved configurations of where connections may be designed, other than at a single faceplate location. This enables improved design and packaging to achieve smaller yet powerful devices suitable for all patient needs. In one embodiment, an implantable cardioverter defibrillator device is provided which has at least one capacitor for storing and delivering electrical energy on demand. The capacitor has at least a 30 Joule capacity and a volumetric energy density of at least about 5 Joules per cubic centimeter. The at least one capacitor has outer surfaces which conform in shape to adjacent components or housing walls. The outer surfaces comprise a plurality of ceramic chips or similar structure which may include at least two chips having a different shape or aspect ratio. The device volume of the above implantable cardioverter defibrillator may also be less than about 5 cubic centimeters.

Thus, embodiments of a complex shaped ceramic capacitor are disclosed. One skilled in the art will appreciate that the present invention can be practiced with embodiments other than those disclosed. For example, the capacitor may be formed in an assembly of a plurality of sub-component layers or chips, or by other means of forming different shapes. The disclosed embodiments are presented for purposes of illustration and not limitation, and the present invention is limited only by the claims that follow.

The invention claimed is:

1. An implantable cardioverter defibrillator having at least one capacitor manufactured by a process including the following method steps:
   a. providing at least one print pattern for a capacitor to a first layer of cast tape formed by a casting and screen printing process;
   b. applying a first layer of electrode material onto portions of the print pattern;
   c. reversing the print pattern having said electrode material by 180°;
   d. applying a second layer of cast tape having a print pattern over the first layer of electrode material; and
   e. creating a stack by applying alternating layers of cast tape and electrode material by repeating steps b., c., and d., above so that the rotation and applying steps creates adjacent terminals on the same side of the capacitor.

2. The method of claim 1, further comprising the step of laminating the stack at high pressure.

3. The method of claim 2, further comprising the step of removing a portion of the stack comprising at least one print pattern of a capacitor forming a capacitor stack.

4. The method of claim 3, further comprising the step of cutting the capacitor stack into at least two parts.

5. The method of claim 4, further comprising the steps of locating the center of the print pattern and cutting the capacitor stack in half through the center of the stack between upper and lower surfaces to create half portions.

6. The method of claim 5, in which the step of providing the at least one print pattern includes creating a generally D-shaped print pattern with a generally U-shaped area along a centerline of the pattern in which no electrode is material is applied.

7. The method of claim 5, in which the half portion of the stacks are then processed, joined, partially rotated and then reassembled to form new full D-shaped capacitor stacks in which the orientation of the half portions is different than in the original half portions.

8. The method of claim 1, in which the step of providing the at least one print pattern includes creating a generally U-shaped area along a centerline of the pattern in which no electrode is material is applied.

9. The method of claim 1 wherein the number of layers of cast tape and electrode material ranges from about 20 to about 50.

10. A capacitor manufactured by a process including the following method steps:
    a. providing a plurality of print patterns for at least one capacitor to a first layer of cast tape formed by a casting and screen printing process;
    b. applying a first layer of electrode material onto portions of the print patterns;
    c. reversing the print pattern by 180°;
    d. applying a second layer of cast tape having a print pattern over the first layer of electrode material;
    e. creating a plurality of stacks applying alternating layers of cast tape and electrode material by repeating steps b., c., and d., above for each stack so that the rotation and applying steps creates adjacent terminals on the same side of the capacitors;
    f. laminating the stacks at high pressure;
    g. removing a portion of at least one of the stacks in a manner which alters the shape of a portion of the at least one stack from the original print pattern;
    h. locating a cut line on the print pattern in each stack and cutting the capacitor stacks through the cut line between upper and lower surfaces to create portions of the pattern in which at least two chips have different sizes; and
    i. processing the chips, and partially rotating at least some of the chips and then assembling various chips to form new full capacitor stacks in which the orientation of the portions is different than in the original portions and the shape of the new full capacitor stacks are different than in the initial print pattern.

11. The capacitor of claim 10, in which the shape of the new full capacitor stacks includes compound surfaces shaped for conformal fit with another component or housing.

12. The capacitor of claim 10 wherein the number of layers of cast tape and electrode material ranges from about 20 to about 50.

13. A tape process method of manufacture for a capacitor for use in implantable medical devices, the method comprising:
    casting a wet film for casting tape on a surface;
    forming a desired thickness of the film;
    drying the film;
    applying a print pattern to the film;
    applying a first layer of electrode material onto portions of the print pattern;
    reversing the print pattern having said electrode material by 180°;
    casting a second wet film over the first layer of electrode material; and
    applying alternating layers of wet layers and electrode materials with reversing the print patterns by 180° between each layer application to form a stack having lenticular layers to build the capacitor of a desired capacitance value.

14. The method of claim 13 wherein one of a wet cast, wet printing and waterfall process is used in lieu of the tape process.

15. The capacitor of claim 13 wherein the number of layers of cast tape and electrode material ranges from about 20 to about 50.

* * * * *